(12) United States Patent
Blackwell

(10) Patent No.: US 6,387,982 B1
(45) Date of Patent: May 14, 2002

(54) SELF ETCHING ADHESIVE PRIMER COMPOSITION AND POLYMERIZABLE SURFACTANTS

(75) Inventor: Gordon Brian Blackwell, Constance (DE)

(73) Assignee: Dentsply DeTrey G.m.b.H. (DE)

( * ) Notice: Subject to any disclaimer, the term of this patent is extended or adjusted under 35 U.S.C. 154(b) by 0 days.

(21) Appl. No.: 09/198,315

(22) Filed: Nov. 23, 1998

(51) Int. Cl.[7] ............................................. A61K 6/083
(52) U.S. Cl. ..................... 523/118; 524/547; 524/556; 524/801; 524/807; 524/832; 526/227; 526/278
(58) Field of Search .................... 523/118; 524/547, 524/556, 807, 832, 801; 526/277, 278

(56) References Cited

U.S. PATENT DOCUMENTS

| | | | |
|---|---|---|---|
| 3,996,180 A | * 12/1976 | Kane | 524/801 |
| 4,031,053 A | * 6/1977 | Bunkley et al. | 524/833 |
| 4,230,772 A | * 10/1980 | Swift et al. | 428/442 |
| 4,358,476 A | 11/1982 | Zimmer et al. | 427/44 |
| 4,359,564 A | * 11/1982 | Merritt et al. | 526/260 |
| 4,554,336 A | 11/1985 | Kidd et al. | 526/301 |
| 4,872,936 A | 10/1989 | Engelbrecht | 156/307.3 |
| 5,065,786 A | * 11/1991 | Akahane et al. | |
| 5,243,069 A | * 9/1993 | Emmons | 526/260 |
| 5,264,513 A | 11/1993 | Ikemura et al. | 526/318 |
| 5,338,773 A | 8/1994 | Lu et al. | 523/116 |
| 5,362,773 A | 11/1994 | Brindoepke et al. | 523/415 |
| 5,405,618 A | * 4/1995 | Buttery et al. | 522/71 |
| 5,498,643 A | 3/1996 | Antonucci et al. | 523/118 |
| 5,534,562 A | 7/1996 | Jensen et al. | 523/118 |
| 5,563,214 A | * 10/1996 | Share et al. | 524/809 |
| 5,629,361 A | 5/1997 | Nakabayashi et al. | 523/118 |
| 5,658,963 A | 8/1997 | Qian et al. | 522/14 |
| 5,670,559 A | 9/1997 | Zeng et al. | 523/118 |
| 5,690,840 A | 11/1997 | Antonucci et al. | 216/34 |
| 5,708,052 A | 1/1998 | Fischer et al. | 523/116 |
| 5,726,217 A | 3/1998 | Ichikawa | |
| 5,733,968 A | 3/1998 | Moszner et al. | 524/779 |
| 5,739,177 A | 4/1998 | Ohno et al. | 523/118 |
| 5,795,926 A | * 8/1998 | Niessner et al. | 524/801 |
| 5,922,278 A | * 7/1999 | Mitra et al. | 524/547 |
| 5,977,194 A | * 11/1999 | Mork et al. | 521/61 |
| 5,977,201 A | * 11/1999 | Johns et al. | 522/111 |

FOREIGN PATENT DOCUMENTS

| | | |
|---|---|---|
| EP | 0 381 862 | 8/1990 |
| EP | 0 471 972 | 2/1992 |
| EP | 0 301 516 | 9/1992 |
| EP | 0 572 227 | 12/1993 |
| EP | 0 712 622 | 11/1995 |
| JP | 7-48219 | 2/1995 |
| WO | WO 93/12760 | 7/1963 |
| WO | WO 95/20937 | 8/1995 |
| WO | WO96/23480 | 8/1996 |

\* cited by examiner

*Primary Examiner*—Peter Szekely
(74) *Attorney, Agent, or Firm*—Dale R. Lovercheck; James B. Bieber

(57) ABSTRACT

The invention provides a self etching adhesive dental primer composition, a method of use of the primer composition and a product formed from the primer. The dental product is formed from the primer composition which includes water, surfactant and polymerizable material in suspension in the water. The polymerizable material includes monomers which are water immiscible. Preferably the monomers have an average molecular weight less than 1000. The primer composition is used by applying the composition to unetched dental tooth enamel and the polymerizable material is polymerized to form a dental product having adhesion to the enamel of more than 13 MPa. Improved surfactants which contain at least one ethenically unsaturated polymerizable group are provided in accordance with the invention. Surfactants of the present invention copolymerize with and become an integral part of any polymerizable resin matrix in which they are incorporated. This prevents migration of the surfactant through the matrix or slow leaching-out through the interfaces, and brings advantages of biocompatibility and stability of the physical properties of the cured matrix. In addition, the surfactant becomes a permanent part of the matrix, and forms part components of the matrix.

15 Claims, No Drawings

SELF ETCHING ADHESIVE PRIMER COMPOSITION AND POLYMERIZABLE SURFACTANTS

The invention relates to dental adhesive primers. In particular, the invention provides a self-etching dental adhesive primer composition and polymerizable surfactants. The primer composition is used in a method of coating a water insoluble polymerizable monomer mixture on a tooth or bone substance. The primer composition is useful as an adhesive or adhesion promoter to affix dental filling materials or bone cements to tooth material. Other uses include forming a protective film on the tooth or bone, or for fixing bone cements in position. The composition essentially comprises an emulsion of water immiscible polymerizable monomers, oligomers and adhesion promoters in water. By using an emulsion of the polymerizable substances in water the need for volatile organic solvents is avoided and biocompatability is enhanced. A further advantage is that independent of the resin phase, the pH of the aqueous phase can be adjusted to provide a self-etching action on the tooth and bone substance, thus enhancing adhesion of the layer to the tooth or bone without requiring a separate etching step. The composition preferably further comprises initiators, accelerators, and inhibitors as often used in unsaturated polymerizable mixtures. Further, the composition preferably comprises surfactants and colloidal silica particles to aid in the formulation of an emulsion and to help keep this stable. Optionally, fluoride releasing agents, bactericidal substances or medicinally beneficial materials may also be included in either aqueous or the resin phase of the composition. The emulsion will typically contain droplets with diameters of less than 30 microns of the polymerizable monomers, oligomers and adhesion promoters. More preferably most of the droplets have a diameter less than 10 microns. Preferably a portion of the droplets will have a diameter less than 1 micron. On applying the composition to the tooth or bone substance the film may first be left for a few seconds to allow an etching action to occur. The water may then be gently blown away, whereby the droplets of polymerizable monomers, oligomers and adhesion promoters coalesce to form a continuous film. No washing of the treated surface is required.

The present invention provides surfactants containing polymerizable monomers for use in compositions. The surfactants are able to polymerize into the matrix to become part of the polymer, and are thereby immobilised. Applications for surfactants containing polymerizable monomers are wide and varied, and include for instance paints and coatings, inks, and glues, particularly those where the coating, ink, or glue is cured by exposure to light. In particular, the surfactants of the present invention are useful in dental restorative materials.

BACKGROUND OF THE INVENTION

Prior art water-soluble hydrophilic materials form very weak spongy polymers, and have undesirable physical characteristics in the cured film layer. The polymerizable resin mixtures and composites used for the repair and replacement of tooth substance, or for the fixation of prosthesis into bone do not adhere of themselves to the tooth or bone substance, and some means is needed to keep them in place. This has long been a problem, and various methods have been developed to overcome it. Initially the attachment method was purely mechanical, and in dental practice large volumes of tooth had to be drilled away to provide sufficient anchorage to keep the filling material in place. U.S. Pat. No. 4,514,342 discloses adhesion promoters such as PENTA. U.S. Pat. No. 5,645,429 discloses primer and adhesive combined into one formulation. Although this has excellent adhesion to dentin, adhesion to unetched enamel is lower than when the enamel is first etched. Therefore when the highest adhesion to both dentin and enamel is required the enamel still needs to be etched, and the steps needed to produce an adhering tooth filling material are first etching, next applying the combined primer/adhesive, and finally applying the filling material. Although this is a considerable improvement over two component adhesives, it still requires considerable time and skill on the part of the dentist. After the tooth material has been etched, for instance, it has to be totally protected from contamination with body fluids. If contamination does occur, then the etching procedure has to be repeated. It would therefore be a further advantage if the etching procedure could be combined with the application of the adhesive, since this would not only save the dentists time, but would also eliminate one of the steps in which contamination of the prepared surface is possible. This would in consequence lead to a further improvement in the quality and reliability of the completed restoration of the tooth. These problems of prior art dental primer/adhesive are overcome by the composition, method and product of the present invention.

Surfactants are used in a wide range of purposes, often to help liquids to spread out over a surface, or to help otherwise incompatible components to mix and remain as a homogenous formulation. Often, a surfactant has to do both simultaneously. A common example is washing-up liquid, which enables water to spread out on a greasy surface, and also helps to keep the loosened globules of fat suspended in the water. There are many types of surfactant, but all consist basically of a hydrophobic part and a hydrophilic part. Both the hydrophobic and hydrophilic parts can comprise either a long chain, or a compact "head". In addition, the hydrophilic part can be either ionic or non-ionic. There are many possible ways of combining these different hydrophobic and hydrophilic parts, leading to a wide range of possible surfactants. Another common use of surfactants is in cosmetic creams and medicaments, where they are used to keep for instance paraffin oil or other water insoluble materials suspended in an aqueous base. This type of formulation is also known as an oil in water emulsion. By suitable choice of surfactant it is also possible to keep droplets of water suspended and stable in a non water miscible oil, and this is known as a water in oil emulsion. Surfactants are also often used in paints, glues, and other surface coatings, and sometimes two or more surfactants are used together to provide optimum surface wetting properties as well as optimum emulsion stability. With a paint, or other coating that is intended to dry, it is usually desirable that when the coating is dry, the surfactant is de-activated or immobilised in some way. In the case of coatings, leaching of the surfactant or its migration towards the air—coating interface can produce discoloration, whereas migration and concentration at the hard surface to which the paint or coating is attached can cause the coating to come loose from the surface to which it is adhering. In essence a surfactant is a material which contains both a non polar hydrophobic end and a polar hydrophilic end, and which is able to form an interface between two surfaces of differing polarity. The word "surfaces" is used broadly when applied to surfactants, and can mean either two solid surfaces, two liquid surfaces, or one solid and one liquid surface. However, not all materials which have both polar and non-polar ends are effective surfactants. The non polar end, for instance has to be large enough to keep it firmly attached to a non polar solid surface, or to keep it directed towards or within the surface of a non polar liquid surface. Likewise, the polar end has to be large enough to keep it within the polar environment. The ratio of the polarity of the hydrophilic end to the non polarity of the hydrophobic end also has to be correct and ideally should be optimised for each application. Because it is often hard to find one single surfactant with the ideal properties, mixtures of two or more surfactants are often used in practical formulations. The polar—nonpolar properties of the surfactants are approximately additive, and by choice of a suitable ratio of suitable surfactants a wide range of applications can be covered. Many successful surfactants are known, for instance those known as the Spans, which consist of esters of long chain fatty acids with sorbitan. By changing the length of the fatty acid and the number attached to the sorbitan group, a range of surfactants with varying properties is obtained. Another group of commonly used surfactants are those known as the Tweens. These also consist of esters of fatty acids with sorbitan, but with the addition of a polyethylenoxide chain attached to the sorbitan. By changing the length and number of the fatty acids and also the length of the polyethylenoxide chain, a further range of surfactants is produced. Yet a further group of surfactants comprises esters of fatty acids directly with polyethylenoxide. By varying both the fatty acid and the length of the polyethylenoxide chain surfactants with varying properties can be produced. The surfactants described above all come within the general group known as non—ionic surfactants. However, surfactants may also be produced by combining non-polar groups with polar ionic groups such as phosphates, sulfates, quaternary amines, and carboxylic groups. A well known example of this class is sodium lauryl sulphate. However, none of the above surfactants contains an easily polymerizable group which would enable it to be incorporated permanently into the matrix of which it is part. Water dispersible polyurethanes containing polyalkylene oxide polyether chains and sulfonate groups are already know, as illustrated in U.S. Pat. No. 4,190,566, U.S. Pat. No. 4,303,774, and U.S. Pat. No. 5,624,758. However these materials do not contain unsaturated polymerizable groups, and are not polymerizable.

OBJECTS OF THE INVENTION

It is an object of the present invention to provide a composition and method for simultaneously etching a tooth or bone surface and deposition of a polymerizable priming resin layer thereon.

It is an object of the invention to provide a self etching adhesive dental primer composition, comprising water, surfactant and polymerizable material in suspension in said water, the polymerizable material comprising monomers, which are water immiscible.

It is an object of the invention to provide a method for coating a tooth comprising forming an emulsion of droplets of water immiscible monomers in water by high shear mixing for at least 5 minutes, applying the emulsion to a surface of a tooth in a patient's mouth and evaporating the water.

It is an object of the invention to provide a dental product formed by providing a self etching adhesive dental primer composition, comprising water, surfactant and polymerizable material in suspension in the water, the polymerizable material comprising monomers which are water immiscible. Preferably at least a portion of the monomers having a moiety selected from the group consisting of phosphoryl and a salt of phosphoryl, the monomers having an average molecular weight less than 1000. The primer is applied to unetched enamel of a dental tooth and polymerizing the polymerizable material to form a dental product having adhesion to the enamel of more than 13 MPa.

It is an object of the invention to provide a compound within the scope of general formula: $(R)_a$—L'—$[R_1]$—L"—$\{X\}_b$, wherein R represents a polymerizable moiety, $R_1$ is a hydrophobic hydrocarbon moiety, X is an ether group, a and b each independently is an integer from 1 to 50, L' is a linking group capable of linking R to $R_1$, L" is a linking group capable of linking $R_1$ to X and neither L' nor L" is a carbon to carbon bond or an ether group.

High shear mixing typically uses a mixing blade rotated adjacent to a stationary plate with small holes therethrough. As referred to herein the rotating blade of the high shear mixer is rotated at about 22,000 revolutions per minute in a container having a volume of about 500 ml. High shear mixing to form compositions in accordance with the invention is preferably for at least 1 minute, more preferably for at least 3 minutes and most preferably for about 5 minutes.

As used herein "PENTA" refers to dipentaerythritolpentacrylate phosphoric acid ester, prepared according to Example 2 of U.S. Pat. No. 4,816,495.

For convenience and easy reference herein, the various surfactants have been given a code such as G750, whereby G stands for glycerol dimethacrylate, and 750 is the mean molecular weight of the polyethyleneglycol chain moiety used.

As used herein BHT refers to 2,6-di-tert-butyl-4-methyl phenol.

As used herein FTIR refers to Fourier—Transform Infra red Spectroscopy.

BRIEF SUMMARY OF THE INVENTION

The invention provides a self etching adhesive dental primer composition, a method of use of the primer composition and a product formed from the primer. The dental product is formed from the primer composition which includes water, surfactant and polymerizable material in suspension in the water. The polymerizable material includes monomers which are water immiscible. Preferably at least a portion of the monomers have a moiety selected from the group consisting of phosphoryl and a salt of phosphoryl. The monomers have an average molecular weight less than 1000. The primer is used by applying to unetched dental tooth enamel and the polymerizable material is polymerized to form a dental product having adhesion to the enamel of more than 13 MPa.

The invention provides polymerizable surfactant compounds within the scope of general formula:

wherein R represents a polymerizable moiety,
$R_1$ is a hydrophobic hydrocarbon moiety,
X is an ether group,
a and b each independently is an integer of 1, or more and
L' is a linking group capable of linking, R to $R_1$
L" is a linking group capable of linking $R_1$ to X and neither L' nor L" is a carbon to carbon bond.

DETAILED DESCRIPTION OF THE INVENTION

Previous attempts to produce polymerizable aqueous formulations have all involved water-soluble monomers and polymers. It has now been found possible to produce stable suspensions of water immiscible monomers in water, in which the insoluble monomers are present as tiny, separate droplets suspended in water. The size of the largest dimension of each droplet of resin in the suspension is preferably less than 30 microns and more preferably less than about 10 microns. Such a suspension of a water immiscible component in water is generally referred to as an oil-in-water emulsion. Preferably, one or more surfactants or other surface active agents are added either singly or in combination to help keep the suspension stable. Because the restriction of water solubility of the resin is removed, the wide range of monomers commonly used in dentistry can be employed in the present invention, and the physical characteristics of the cured resin layer can adjusted or optimized without restriction. The pH of the aqueous phase can be adjusted independently of the resin phase as required.

A wide range of ethenically unsaturated monomers, polymerization initiators, and surfactants are useful in compositions in accordance with the invention.

Bond Strength to Tooth Dentin and Enamel is Measured Herein Including the Examples as Follows Human extracted teeth without significant anatomical alterations, defects or restorations were cleaned and disinfected by soaking in 1% sodium hypochlorite solution for 18 to 24 hours, rinsed, and then stored at from 1 to 8° C. in 1% sodium chloride I water (saline solution) until used within six months.

Teeth were prepared for adhesion to dentin by hand sanding them using wet 300 grit silicon carbide paper, to expose an area of dentin at a plane just below the original interface between the enamel and the dentin. This area was then polished by hand sanding with wet 600 grit silicon carbide paper. The teeth were kept in water until used within 1 to 12 hours.

When adhesion to enamel was to be tested, the teeth were chosen so that an approximately flat area of enamel about 5 mm in diameter was present. This area was washed and cleaned using wet 1200 grit silicon carbide powder and a bristle brush rotating in a dental handpiece. The teeth were then used within 6 hours as below.

The surface to be adhered to was dried lightly with a paper tissue, and the treatment solution or emulsion applied using a felt applicator as supplied by DENTSPLY for 10 to 30 seconds and then the remaining solvent or water was evaporated by gently blowing with a stream of dry oil free air. The layer of remaining resin was light cured by irradiating it for ten seconds with light from a dental light curing unit having a minimum output of 350 milliwatt/square centimeter in the 500 to 500 nm wavelength range (for instance a Spectrum curing unit sold by DENTSPLY International Inc.). A portion of plastic straw of 5 mm internal diameter and about 4 mm long was placed end on the prepared surface and filled with a light curing dental filling material (Spectrum™ DENTSPLY International Inc.). Finally, the filling material was cured by irradiating for forty seconds from the exposed end with the dental light.

The prepared samples were stored for 24 hours in water at 37° C. before being thermocycled 500 times between water baths held at 5° C. and 55° C. with a dwell time in each bath of 20 seconds. The thermocycled samples were then left in water at 37° C. overnight before being tested in shear using a Zwick universal testing machine model Z010 with a cell having a maximum load of 500 Newtons, a crosshead speed of 1 mm per minute and a 2 mm diameter chisel. The chisel has a tip point formed at the lower end by grinding and positioning a planar surface across the end of the cylinder at a 45 degree angle to the central axis of the cylinder. In test position, the tip point of the chisel was applied against the composite. Each tooth was mounted vertically in plaster for the test. A minimum of six samples were prepared for each test, and the mean adhesion was calculated.

In the examples below, Span 80 (manufactured by Atlas Powder Company) is sorbitan monooleate, commercially available from many sources including Adrich, and Tween 80 (manufactured by Atlas Powder Company) is polyoxyethlene(20)-sorbitan monooleate, also available commercially from many sources, including Aldrich.

Surfactants of the present invention have polymerizable groups such as hydroxyethyl methacrylate, hydroxypropyl methacrylate, glycerol dimethacrylate, pentaerythritol triacrylate and the like which have been attached via urethane linkages and a hexyl, cyclohexyl, pentyl, octyl or other hydrocarbon group moiety to polyethylenegycol chains of varying length and numbers. The methacrylate or acrylate moiety (hereafter written as (meth)acrylate) together with the hydrocarbon group moiety form a non polar hydrophobic end, while the polyethyleneglycol chain forms a polar hydrophilic end. By varying the number of (meth)acrylate groups and the length or number of the polyethyleneglycol or chains, surfactants with a wide variety of properties may be produced. In addition to the (meth)acrylate groups, other non polar groups such as fatty acids may also be incorporated to provide an even more hydrophobic end when this is required. The polyethyleneglycol chain may further be broken in several short chains if desired. A common method of determining the suitability of a surfactant for a particular use is to measure or calculate its HLB value. There are several methods to estimate the HLB value of materials, but for surfactants containing polythylenglycol chains, the HLB value is approximately given by the relationship:

HLB is equal to the mole percent of hydrophilic group divided by five.

For materials not containing a polythylenglycol chain or chains the HLB value of a material may be approximately calculated by adding together the so called "group number" of the individual chemical groups contained in the compound. In this case the HLB value is approximately given by the relationship:

HLB is equal to seven added to the sum of the hydrophilic groups numbers and the sum of the lipophilic group numbers These methods are described in, for example, "Surfactant Systems, D. Atwood and A. T. Florence, published by Chapman and Hall". The HLB values given below were calculated by one of these methods, and are meant only as a rough guide to the properties of the surfactants described.

The invention provides polymerizable surfactant compounds within the scope of general formula:

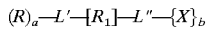

wherein R represents a polymerizable moiety, $R_1$ is a hydrophobic hydrocarbon moiety, X is a ether group, a and b each independently is an integer of 1, or more and L' is a linking group capable of linking, R to $R_1$ L" is a linking group capable of linking $R_1$ to X and neither L' nor L" is a carbon to carbon bond.

Use of the polymerizable surfactants as emulsion stabilisers.

Although the polymerizable surfactants have a multitude of possible uses, they are preferably used as stabilisers for emulsions of water immiscible monomers in water, and also to aid in the spreading out of such monomers onto a hydrophilic surface. Specifically, the emulsions are preferably adhesives and coatings. Although surfactants such as the Tweens and Spans are already available and are capable of providing stable emulsions and aiding in the spreading of monomers on a hydrophilic surface, they are not ideal. As described earlier, these surfactants are not polymerizable and are able to leach out of the cured formulation. They will thereby tend to concentrate at the interface between the solid which is to be adhered to and the surface of the coating or adhesive, and facilitate a loosening of the coating or adhesive. This is generally not desirable. In addition, because the properties of the available surfactants are not ideal, high levels must be used in the formulations in order to obtain a stable emulsion, thus exacerbating the problem of their leaching out. The surfactants of the present invention are often required at lower levels to obtain a stable emulsion. The use of these surfactants is not limited to those illustrated in the further examples below, and these examples serve only to further demonstrate the present invention.

PREPARATION OF SURFACTANT G750

EXAMPLE 1

11.1 grams Isophoronediisocyanate was stirred with 38.25 grams polyethylene glycol monomethylether 750, (mean molecular weight 750) and dibutyl tin dilaurate (0.25 grams) at 40° C. for one hour. After this time an FTIR showed that the —OH group of the polyethylene glycol monomethylether (PEGME) 750 had totally reacted, and a new peak due to —NH was apparent. 11.4 grams Glycerine dimethacrylate was added together with 0.05 grams BHT polymerisation inhibitor and the mixture stirred at 30° C. for 6 hours. An FTIR spectrum showed a small peak due to the isocyanate group still present, so a further 0.4 grams of PEGME 750 was added. After stirring further an FTIR showed that reaction was complete. The polymerizable surfactant (G750) product was a white, soft sticky solid at room temperature, partially soluble in water to give a light foam on shaking. The material had a melting range of about 35–37° C. The HLB value is calculated to be approximately 12.5

PREPARATION OF SURFACTANT G2000

EXAMPLE 2

5.6 grams Isophoronediisocyanate was stirred with 50 grams polyethylene glycol monomethylether 2000 (mean molecular weight 2000) and warmed to about 60° C. until the PEGME melted. 0.25 grams Dibutyl tin dilaurate was added and the mixture stirred further. A clear liquid was formed which solidified on cooling. This was warmed again to 65° C., 0.05 grams of BHT was added, followed by adding 5.7 grams of glycerine dimethacrylate. The mixture was heated to 90° C. and stirred for about 2 hours, after which an FTIR showed that all the isocyanate had been consumed. The product was a white hard waxy solid, partially soluble in water to give a light foam on shaking. The material had a melting range of about 49–51° C. The HLB value is calculated to be approximately 16.

PREPARATION OF SURFACTANT G5000.

EXAMPLE 3

The method of Example 2 was repeated except for the amount of each component, 75 grams polyethylene glycol monomethyl ether with a mean molecular weight of about 5000 was used, together with 3.33 grams of isophorone diisocyanate, 0.1 gram of dibutyl tin dilaurate. After completion of this first reaction, 3.5 grams glycerol dimethacrylate and 0.05 grams BHT were added. As in example 2, the mixture was stirred at 90° C. for about 2 hours after which the reaction was complete. The polymerizable surfactant (G5000) product was a hard waxy solid, partially soluble in water to give a light foam on shaking. The material had a melting range of about 58–60° C. The HLB value was calculated to be approximately 18.

PREPARATION OF SURFACTANT HP2000

EXAMPLE 4

5.6 grams Isophorone diisocyanate and 50 grams polyethylene glycol monomethyl ether 2000 were put in a flask and warmed together at 60° C. until homogenous. 0.25 grams dibutyl tin dilaurate was then added and the mixture stirred and heated at 65° C. for 5 hours. After this time an FTIR showed that the —OH groups of the polyethyleneglycol monomethyl ether had totally reacted. 3.6 grams hydroxypropylmethacrylate and 0.05 grams BHT were added and the mixture stirred approximately one hour. After this time an FTIR spectrum showed that the —OH of the hydroxypropylmethacrylate and the NCO group had totally reacted. A polymerizable surfactant (HP2000) product, as a white waxy solid, was obtained which had a melting range of 50–52° C. The HLB value was calculated to be approximately 17.

PREPARATION OF SURFACTANT HP750

EXAMPLE 5

The reaction of Example 4 was repeated except for using an equimolar amount of monomethyl ether 750 in place of the monomethyl ether 2000 and, due to the lower melting point of the monomethyl ether 750, the mixture was stirred at 50° C. instead of 65° C. The polymerizable surfactant (HP750) product material formed had a melting range of about 31.4° C.–33.1° C. The HLB value was calculated to be approximately 13.

PREPARATION OF SURFACTANT HE2000

EXAMPLE 6

The reaction of Example 4 was repeated except for using an equimolar amount of hydroxyethyl methacrylate in place of the hydroxypropylmethacrylate to form a polymerizable surfactant (HE2000) product. The HLB value was calculated to be approximately 17.

Preparation of an adduct between isophorone diisocyanate, polyethylene glycol monomethyl ether 2000, and pentaerythritol diacrylate stearate.

EXAMPLE 7

30 gram polyethylene glycol monomethyl ether with a mean molecular weight around 2000 was melted at about 60° C. and 3.3 grams isophorone diisocyanate added. After half an hour 0.1 gram dibutyl tin dilaurate was added and the mixture heated and stirred for 3 hours. After this time an FTIR showed no —OH groups were left. 0.05 grams BHT was added followed by 7.74 grams pentaerythritol diacrylate stearate. The mixture was warmed and heated at 50° C., then a further 0.1 grams of dibutyl tin dilaurate was added. The mixture was heated a further 3 hours at 60° C. after which an FTIR showed that all the isocyanate had been consumed. The product was a hard waxy solid, insoluble in water but easily soluble in a range of methacrylate monomers. The material had a melting range of about 52–54° C. The HLB value was calculated to be approximately 15.

Preparation of an adduct between isophorone diisocyanate, pentaerythritol ethoxylate (mean MW 270) and glycerol dimethacrylate.

EXAMPLE 8

11.1 grams Isophorone diisocyanate was placed in a flask, and 11.4 grams glycerol dimethacrylate and 0.05 grams BHT added with stirring. This was followed by 0.05 grams dibutyl tin dilaurate, after which the mixture was stirred at room temperature for one hour. After this time the mixture had become more viscous and an FTIR spectrum showed that the —OH from the glycerol dimethacrylate had fully reacted. The mixture was warmed to 40° C. to reduce the viscosity, and 13.5 grams pentaerythritol ethoxylate (mean MW 270, approx. 4 ethoxy units) was added with stirring. The mixture was stirred and held at 45° C. for 2 hours, after which time an FTIR spectrum showed that all of the isocyanate had been consumed. Because the pentaerythritol ethoxylate contains four —OH groups, these still showed strongly in the FTIR spectrum. The material was warmed briefly to 60° C. to reduce the viscosity and poured out into a bottle. The product was a colourless highly viscous honey-like material, which was insoluble in water, but soluble in a range of methacrylate resins. The HLB value was calculated to be approximately 7.

Preparation of an adduct between isophorone diisocyanate, polyethylene glycol monomethyl ether 2000, and pentaerythritol triallyl ether.

EXAMPLE 9

The procedure of Example 7 was followed, except that pentaerythritol triallyl ether (3.85 gram) was used in place of the pentaerythritol diacrylate stearate. The product was a soft wax like substance. The HLB value is calculated to be about 17.

PREPARATION OF UK21-181-1

EXAMPLE 10

A mixture of monomers was made up for use as a dental adhesive. This was stirred until it was homogenous.

| | |
|---|---|
| Urethane resin | 53.5% |
| PENTA | 24.165% |
| Urethane resin R5-62-1 | 15.127% |
| Bisphenol-A-dimethacrylate | 2.852% |
| Camphorquinone | 0.972% |
| Dimethylaminobenzoic acid, ethyl ester | 2.9% |
| 2,6-Ditertiarybutyl-4-methyl-phenol | 0.483% |

This resin mixture (UK21-181-1) was used in some of the Examples below.

PREPARATION OF UK-21-30-1

EXAMPLE 11

20 grams of the resin mixture UK21-181-1 formed by following the procedure of Example 10, 80 grams of deionized water, and 1.01 grams of Aerosil A200 sold by Degussa were mixed and treated with a high shear mixer for about 2 minutes. Two phases where formed, which would not disperse. The surfactants Span 80 and Tween 80 were then added drop-wise and the mixture retreated with the high shear mixer at about 22,000 rpm for two minutes. The mixture was investigated for stability of the suspension, and if necessary to maintain the stability of the suspension more Tween and Span was added and the mixture treated again with the high shear mixing at about 22,000 rpm for two minutes. Only after 2 grams of Tween and 2 grams of Span had been added was a homogenous suspension was formed, which remained stable for at least the period of observation of 3 days. A heavy foam was formed on the surface of the emulsion. The product is brushed onto unetched dental tooth enamel. Adhesion of the product to enamel is shown in Table 1 below.

PREPARATION OF UK-21-33-1

EXAMPLE 12

15 grams of the resin mixture UK 21-181-1 formed by following the procedure of Example 10, and 35 grams deionized water was mixed in a high shear mixer at 22,000 rpm for three minutes. A cloudy suspension was formed but this separated out over a period of a few minutes into a lower resin phase and an upper aqueous phase. Tween 80 and Span 80 surfactants were added drop-wise, and the mixture stirred with a high speed emulsifier. Only after addition of 3.9 grams Tween 80 and 3.8 grams Span 80 was a stable emulsion formed. A heavy foam formed on the surface of the emulsion which made effective emulsification difficult. However the suspension remained stable for several hours, and was examined under a microscope. This showed that many spherical droplets were present with a diameter of under 1 micron, but that a few droplets with a diameter up to about 30 microns diameter also existed. The suspension was spread out on a slide glass to give a milky layer. The droplets were observed with a microscope and it was seen that as the water evaporated, the droplets coalesced to give a continuous film of resin and the appearance of the layer simultaneously changed from milky to clear. This layer could be cured by shining a light on it.

PREPARATION OF GB8-18-1

EXAMPLE 13

0.5 grams of the polymerizable surfactant formed by following the procedure of Example 1, and 20 grams of the resin mixture UK 21-181-1 formed by following the procedure of Example 10 were warmed together. The surfactant readily dissolved in the resin mixture to give a clear solution. 45 grams of water was added and the mixture shaken. A white emulsion was immediately formed, but some portions of resin were left on the sides of the glass container. The mixture was treated with ultrasound for five minutes and then re-shaken, after which the resin was fully dispersed in the water. This ultra sound and shaking procedure was repeated a further two times. After this a fine white emulsion was formed, which was further treated with a high shear mixer for five minutes. A light foam formed on the surface of the emulsion. Although this initial emulsion was stable for about 2 days, droplets of resin eventually fell to the bottom of the flask indicating that long term stability had not been obtained.

PREPARATION OF GB8-18-2

EXAMPLE 14

The method of Example 13 was repeated except that 1 gram (rather than 0.5 gram) of the polymerizable surfactant product formed by following the procedure of Example 1 was used. An emulsion was easily formed by stirring, but it did not have long term stability.

PREPARATION OF GB8-19-1

EXAMPLE 15

The method of Example 13 was repeated except that 1 gram of the polymerizable surfactant from Example 2 was used. An emulsion was easily formed which was more stable than that in Example 13, but long term stability over a period of several weeks was still not obtained. A light foam formed on the surface of the emulsion.

PREPARATION OF GB8-19-2

EXAMPLE 16

The method of Example 13 was repeated except that 1.5 grams (rather than 0.5 grams of the product formed in Example 1) of the polymerizable surfactant formed by following the procedure of Example 2 was used. An emulsion was easily formed, and stability was better than with Example 15. A light foam formed on the surface of the emulsion.

PREPARATION OF GB8-19-3

EXAMPLE 17

The method of Example 13 was repeated except that 2 grams of the polymerizable surfactant from Example 2 was used in place of the polymerizable surfactants formed by following the procedures of Example 1. An emulsion was easily formed. A light foam formed on the surface of the emulsion. The emulsion was stable for extended periods of more than 1 month.

PREPARATION OF GB8-25-1

EXAMPLE 18

2 grams of the polymerizable surfactant from Example 7 was dissolved in 10 grams of the resin from Example 10 and 40 grams of the water added. The mixture was shaken briefly, after which a white emulsion was obtained. This was treated for 5 minutes with ultrasound, and then for 5 minutes with a Ultra Torrax high speed mixer. No foaming was observed, but a creamy layer formed on the surface of the emulsion.

PREPARATION OF GB8-26-1

EXAMPLE 19

1 gram of the polymerizable surfactant from Example 7 and 1 gram of the surfactant from Example 3 were dissolved in 10 grams of the resin from Example 10 and 40 grams of water added. The mixture was emulsified according to the forgoing procedure. In this case, no foaming occurred, and only a very little creaming was observed. The emulsion was highly stable over long periods.

EXAMPLE 20

20 parts of the resin made as described in Example 10 was dissolved in 80 parts of acetone. Adhesion to enamel was tests as described earlier and results are given in Table 1.

EXAMPLE 21

The procedure of Example 20 was followed except that the enamel was treated with 36% phosphoric acid solution for 30 seconds, washed, and then dried before the procedure of Example 20 was carried out on the enamel. Results are given in Table 1.

TABLE 1

| MATERIAL | Adhesion to enamel MPa | Substrate |
| --- | --- | --- |
| EXAMPLE 11 | 13.9 ± 0.3 | Unetched enamel |
| EXAMPLE 12 | 14.5 ± 7.0 (max. 23.2) | Unetched enamel |
| EXAMPLE 20 | 7.9 ± 3.9 (max 11.6) | Unetched enamel |
| EXAMPLE 21 | 19.35 ± 3.0 | Etched enamel |

Thus, the compositions of Examples 11 and 12 provide adhesion to unetched enamel of 13.9 MPa and 14.5 MPa (maximum value 23.2 MPa), almost twice as high as the 7.9 MPa of the composition of Example 20 (maximum value 11.6 MPa). This approaches the value of 19.35 MPa obtained in Example 21 when the enamel was separately etched, and demonstrates a self-etching action on enamel taking place in the procedures of Examples 11 and 12.

EXAMPLE 22

5.7 grams of glycerol dimethacrylate, 5.6 grams of isophorone diisocyanate, 0.05 grams of BHT, and 0.01 gram of dibutyl tin dilaurate were stirred together at 23° C. (room temperature) for two hours. After this time an FTIR spectrum showed that all the —OH groups had reacted. A viscous mixture was obtained to which 11 grams of triethyleneglycol dimethacrylate was added. In a separate flask 75 grams of polyethyleneglycol with a mean molecular weight of 3000 was dissolved in 75 grams of triethyleneglycol dimethacrylate at 60° C. To this flask were added the contents of the first flask with stirring, and the whole mixture was stirred at 60° C. for two hours. After this time an FTIR showed that the —NCO groups had reacted. The mixture was allowed to cool to room temperature when a soft, white, paste-like material was obtained.

EXAMPLE 23

4 grams of the material prepared by following the procedure of Example 22 and 19 grams of the mixture prepared by following the procedure of Example 10 were warmed and mixed together to give a homogenous liquid. 18 grams of water was added and the mixture shaken to give a white emulsion. This was treated with ultrasound for five minutes, then reshaken. The emulsion was then further treated for five minutes with a high shear mixer. The resulting emulsion, containing about 43% resin part, was stable and showed no signs of separation. The droplet size was measured and found to have a mean size of 1.5 microns with 90% of the droplets below 2.9 microns.

EXAMPLE 24

8 grams of the material prepared by following the procedure of Example 22 and 40 grams of the mixture prepared by following the procedure of Example 10 were mixed together to give a homogenous liquid. 20 grams of water were added and the mixture shaken to give a white emulsion. This was treated with ultrasound for five minutes, then reshaken. The emulsion was then further treated for five minutes with a high shear mixer. The resin part was about 70%. The resulting emulsion had a cream-like consistency and was highly stable. Adhesion to dentin was tested as described herein above. The dental composite was found to adhere with a mean strength of 17 MPa. The particle size of the droplets in the emulsion were measured and found to have a mean size of 1.6 microns, with 90% of the droplets below 3.3 microns in size.

The following Comparative Examples are provided for comparison and are not representative of the invention.

COMPARATIVE EXAMPLE 1

2 grams of polyethylene glycol 3000, 2 grams of triethyleneglycol dimethacrylate, 10 grams of the mixture prepared by following the procedure of Example 10 were warmed and mixed together to give a homogenous liquid. 18 grams of water were added and the mixture shaken to give a white emulsion. This was treated with ultrasound for five minutes, then reshaken. The emulsion was then further treated for five minutes with a high shear mixer. However the resin part separated out as soon as mixing stopped, and a stable emulsion could not be achieved. This illustrates that polyethylene glycol alone is not a suitable emulisifier in this composition.

COMPARATIVE EXAMPLE 2

The material formed by following the procedure of Example 7 (the adduct between polyethyleneglycol 2000 monomethyl ether, isophorone diisocyante, and pentaerythritol diacrylate stearate)(1 gram), and 10 grams of the mixture formed by following the procedure of Example 10 were warmed and mixed together until homogenous. [2-(methacryloyloxy)ethyl]trimethylammonium chloride (75% aqueous solution, available from Aldrich) (1.33 grams) and 18 grams of water were added and the mixture shaken vigorously. After treatment with ultrasound the mixture was then treated with a high shear mixer for 5 minutes. The resin part quickly separated out when stirring ceased and a stable emulsion could not be achieved. Since a stable emulsion was previously easily prepared using the material from Example 7, this illustrates the strong destabilizing effect of quaterniary amines in this composition.

COMPARATIVE EXAMPLE 3

The method of Example 17 was repeated except that 0.1 grams of cetylamine hydrofluoride was dissolved in the resin mixture before addition of the water. In this case the resin part quickly separated out and, unlike Example 17, a stable formulation was not achieved. This again illustrates the strong destabilizing effect of quaterniary amines.

PREPARATION OF GB8-21-1

COMPARATIVE EXAMPLE 4

The method of Example 13 was repeated except that 2 gram of polyethyleneglycol monomethyl ether 2000 was used in place of the polymerizable surfactant. However the resin phase separated from the water as soon as mechanical agitation ceased, and it was not possible to obtain an emulsion. This demonstrates that the polyethyleneglycol monomethyl ether 2000 itself is not a suitable emulsifier in this application.

In accordance with a preferred embodiment of the invention is provided a self etching adhesive dental primer composition, comprising water, surfactant and polymerizable material in suspension in the water. The polymerizable material comprises monomers. The monomers are water immiscible. At least a portion of the monomers have a moiety selected from the group consisting of phosphoryl and a salt of phosphoryl. The monomers have an average molecular weight less than 1000. Preferably, the composition includes polymerization initiators, such as camphorquinone. Preferably, the composition includes polymerization accelerators, such as tertiary amine compounds. Preferably, the size of the individual droplets of polymerizable monomer suspended in the water is less than thirty microns. Preferably, the polymerization initiator and accelerator are contained within separate suspended droplets of the water immiscible polymerizable monomer or mixture of monomers. Preferably, the monomers are dispersed within droplets having a largest droplet dimension less than 30 microns. More preferably, the monomers are dispersed within droplets having a largest droplet dimension less than 10 microns.

In accordance with a preferred embodiment of the invention is provided a method for coating a tooth comprising forming an emulsion of droplets of water immiscible monomers in water by high shear mixing for at least 5 minutes, applying the emulsion to a surface of a tooth in a patient's mouth and evaporating the water. Preferably, the emulsion of water immiscible monomer in water comprises a self etching adhesive primer dental composition for coating tooth substance or bone comprising water, surfactant and a suspension in the water of a water immiscible polymerizable monomers at least a portion of the monomers having an average molecular weight less than 1000. Preferably, the emulsion of water immiscible monomers comprise PENTA.

In accordance with a preferred embodiment of the invention is provided a self-etching adhesive dental primer formed by high shear mixing for at least 5 minutes. Preferably, the primer is a self etching adhesive primer dental composition for coating tooth substance or bone comprising water, surfactant and a suspension in the water of a water immiscible polymerizable monomers having at least a portion of the monomers having an average molecular weight less than 1000.

In accordance with a preferred embodiment of the invention is provided a dental product formed by providing a self etching adhesive dental primer composition, comprising water, surfactant and polymerizable material in suspension in said water, the polymerizable material comprising monomers which are water immiscible, at least a portion of the monomers having an average molecular weight less than 1000, applying the primer to unetched enamel of a dental tooth and polymerizing the polymerizable material to form a dental product having adhesion to the enamel of more than 13 MPa. Preferably, polymerizable dental restorative material is applied to the dental product.

In accordance with the invention is provided a self etching adhesive dental primer product made by the process comprising high shear mixing a composition, comprising water, surfactant and polymerizable material in suspension in the water. The polymerizable material comprises monomers. The monomers are water immiscible. Preferably at least a portion of the monomers have a moiety selected from the group consisting of phosphoryl and a salt of phosphoryl. The monomers have an average molecular weight less than 1000 to form a self-etching adhesive dental primer product consisting essentially of a suspension of droplets of polymerizable material in water. The droplets have a largest dimension less than 50 microns. The suspension is stable for at least one month at 23° C.

A preferred embodiment of the invention provides a method of simultaneously etching and priming previously unetched tooth enamel which consists essentially of providing a self etching adhesive dental primer composition, comprising water, surfactant and polymerizable material in suspension in the water. The polymerizable material comprises monomers. The monomers are water immiscible. Preferably at least a portion of the monomers have a moiety selected from the group consisting of phosphoryl and a salt of phosphoryl. The monomers have an average molecular weight less than 1000. The self-etching primer is applied to unetched tooth enamel. The polymerizable material is polymerized to form a dental product having adhesion to the enamel of more than 13 MPa. Preferably, the tooth to which the primer is applied is in a patient's mouth.

Polymerizability of the Surfactants

In order to prove that the surfactants could be polymerised, samples of several of the materials from Examples 1 to 8 were stored in an oven at 100° C. All materials melted to give clear liquids, and then gelled over a period of one to two days to give a polymerised mass.

It is apparent from the Examples herein that a wide range of polymerizable surfactants may be made, within the scope of the general formula Figure I:

$$(R)_a\text{—}L'\text{—}[R_1]\text{—}L''\text{—}\{X\}_b \qquad (I)$$

where R is a polymerizable group or groups such as acrylate, methacrylate, vinyl, or vinyl ether $R_1$ is a non polar hydrocarbon moiety such as cyclohexane, isophorone, hexane, trimethylhexane, octane, L' and L" are linking groups, such as ester, urethane, amide, or ether, and may be the same or different X is a hydrophilic group such as polyethylene oxide, polyethyleneglycol, pentaerythritol, pentaerythritol ethoxylate and derivatives of the forgoing.

The number of polymerizable groups (a) must be at least 1, and preferably 2 or more. In order for the material to be an effective surfactant, the multiplier (b) should be such that the total of the X groups have a polarity and water solubilising ability at least equivalent to about four —[CH2—CH2—O]— groups. When X is —[CH2—CH2—O]—, then (b) is more preferably at least 10. The hydrophobic group X can comprise either a single chain as for example in polyethyleneglycol, or multiple chains attached to one central atom as in pentaerythritol ethoxylate.

The groups R, $R_1$, and X can be joined together by methods to join the groups, for example ester, urethane, ethers, or amides linkages can be used within the scope of the present invention.

For instance in Example 1, R is glycerol dimethacrylate where (a) is 2, L' and L" are urethane links, $R_1$ is isophorone, and X is —[CH2—CH2—O]— with (b) approximately 17. One of the possible isomers is shown in general structure II below, where n is approximately 17 and $R^{IV}$ is methyl. When n is approximately 45, the structure shows one possible isomer of the invention of Example 2, while with n approximately equal to 113 a possible isomer of the invention of Example 3 is illustrated. It is understood by those skilled in the art that in reactions such as these, a mixture of products is formed which also contains a mixture of isomers. The reaction conditions can be adjusted for production of the desired compound and isomer, but totally pure compounds with precisely defined structures are usually not obtained. The structures below serve to illustrate compounds within the scope of general structure II.

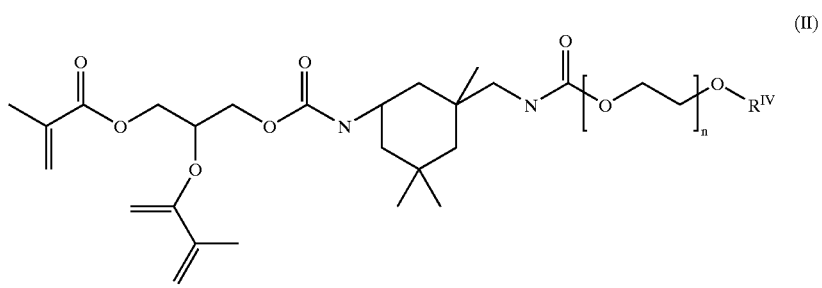

(II)

In Example 4, HP2000, R is hydroxypropylmethacrylate where L' and L" are urethane links, $R_1$ is isophorone, X is —[CH2—CH2—O]— and a is 1, and b approximately 45. Possible isomers of this structure are within the scope of the following general formula III:

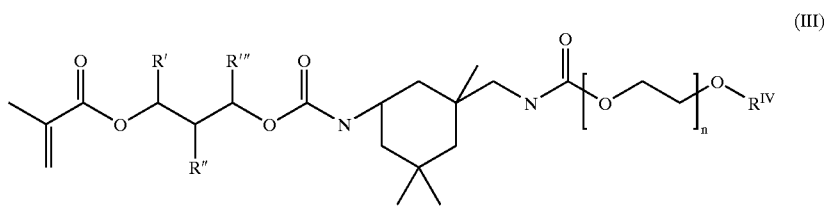

(III)

wherein at least one of R', R" or R'" is methyl, and the others are H, $R^{IV}$ is methyl, and n is approximately 45, and isomers of this structure are also formed and are also included within the scope of the present invention.

The product of Example 5 is within the scope of the structure within the scope of formula III wherein one of R', R" or R'" is methyl, and the others are H, $R^{IV}$ is methyl and n is approximately 17.

Many other groups for X are possible, including pentaerythritol, and pentaerythritol ethoxylate. Similarly, the group P can comprise multiply unsaturated moieties such as pentaerythritol triacrylate, pentaerythritol diacrylate stearate, pentaerythritol triallyl ether.

Preferred compounds within the scope of the general Formula I are compounds within the scope of general formula IV:

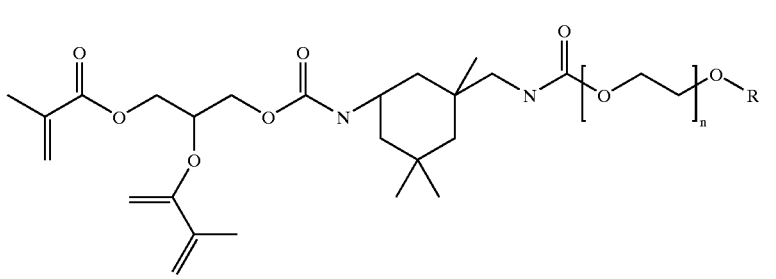

wherein R is H or a carbohydryl group having from 1 to 6 carbon atoms and n is an integer from to 10 to 50.

Preferably in general formula I, R is vinyl ether. Most preferably in general formula I, X comprises —($CH_2$—$CH_2$—O)$_m$— groups wherein m is an integer from 10 to 50. Preferably in general formula I, L' and L" are urethane linkages. Most preferably in general formula I, P is methacrylate or acrylate, X comprises —($CH_2$—$CH_2$—O)$_m$— groups wherein m is an integer from 10 to 50, and L' and L" are urethane linkages.

Additional, preferred compounds within the scope of the general formula I are compounds within the scope of general formula V:

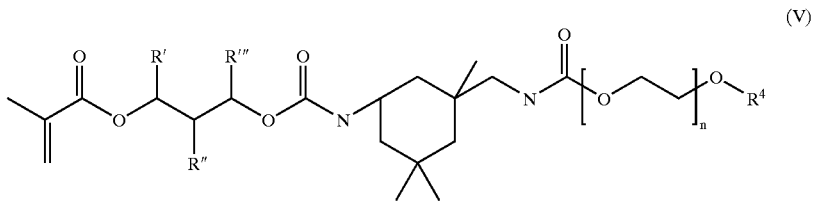

wherein R', R" and R'" each independently is hydrogen or alkyl, $R^4$ is H or methyl and n is an integer from 10 to 50.

Preferably, compounds within the scope of the general formula V is produced by reaction between a hydroxyl (meth)acrylate, a diisocyanate, and a hydroxyl terminated compound selected from the group consisting of polyethyleneoxide and polyethyleneglycol. Preferably, hydroxyl acrylate comprises hydroxy propyl methacrylate. Preferably, the diisocyanate comprises isophorone diisocyanate. Preferably, the hydroxyl acrylate is hyroxyl methacrylate. Preferably, the hydroxyl terminated compound comprises polyethyleneglycol monomethyl ether.

It should of course be understood that while the present invention has been described in considerable detail with respect to certain specific embodiments thereof, it should not be considered limited to such embodiments but may be used in other ways without departure from the spirit of the invention and the scope of the appended claims.

What is claimed:

1. A dental primer composition, comprising water, polymerizable surfactant and polymerizable material in said water as an emulsion, said polymerizable material comprising light curing polymerization initiator and monomers, at least a substantial portion of said monomers effectively being water immiscible, at least a portion of said monomers have a moiety selected from the group consisting of phosphoryl and a salt of phosphoryl, said composition being adapted to bond to dentin with a bond strength of more than 13 MPa.

2. The composition of claim 1 wherein at least one of said monomers comprise a vinyl ether.

3. The composition of claim 1 wherein the polymerization initiator comprises camphorquinone.

4. The composition of claim 1 further comprises polymerization accelerators.

5. The composition of claim 4 wherein the polymerization accelerators are tertiary amine compounds.

6. The composition of claim 4 wherein the polymerization initiator and accelerator are contained within separate suspended droplets of the water immiscible polymerizable monomer or mixture of monomers.

7. The composition of claim 1 wherein said monomers are dispersed within droplets having a largest droplet dimension less than 50 microns.

8. The composition of claim 1 wherein said monomers are dispersed within droplets having a largest droplet dimension less than 30 microns.

9. The composition of claim 1 wherein the size of the individual droplets of polymerizable monomer suspended in the water is less than ten microns.

10. A dental primer for coating tooth substance or bone formed by high shear mixing, comprising water, polymerizable surfactant light curing polymerization initiator and effectively water immiscible polymerizable monomers in said water as an emulsion, at least a portion of said monomers have a moiety selected from the group consisting of phosphoryl and salt phosphoryl, said composition being adapted to bond to dentin with a bond strength of more than 13 MPa.

11. The dental primer of claim 10 wherein said dental primer is formed in a mixer having a stationary plate, said stationary plate having holes therethrough.

12. The dental primer of claim 10 wherein said primer is a coating is on an unetched tooth.

13. A dental primer formed by high shear mixing, comprising water, polymerization initiator, polymerizable surfactant and effectively water immiscible polymerizable monomers in said water as an emulsion, at least a portion of said monomers have a moiety selected from the group consisting of phosphoryl and a salt of phosphoryl, said composition being adapted to bond to dentin with a bond strength of more than 13 MPa.

14. The dental primer of claim 10 wherein said composition is adapted to bond to dentin with a bond strength of more than 13 MPa when light cured by irradiation for ten seconds with light from a dental light curing unit having a minimum output of 350 milliwatt/square centimeter in the 500 to 500 nm wavelength range.

15. The dental primer of claim 10 wherein said composition to bond to dental composite with a bond strength of more than 13 MPa.

* * * * *